(12) United States Patent
Wu

(10) Patent No.: US 9,427,026 B2
(45) Date of Patent: Aug. 30, 2016

(54) ELECTRONIC CIGARETTE FOR CONVENIENT BATTERY CHARGING AND ATOMIZER STARTING

(71) Applicant: SHENZHEN SMACO TECHNOLOGY LIMITED, Shenzhen, Guangdong Province (CN)

(72) Inventor: Yangyang Wu, Shenzhen (CN)

(73) Assignee: SHENZHEN SMACO TECHNOLOGY LIMITED, Shenzhen, Guangdong Province (CN)

( * ) Notice: Subject to any disclaimer, the term of this patent is extended or adjusted under 35 U.S.C. 154(b) by 0 days.

(21) Appl. No.: 14/488,316

(22) Filed: Sep. 17, 2014

(65) Prior Publication Data

US 2015/0000684 A1 Jan. 1, 2015

Related U.S. Application Data

(63) Continuation-in-part of application No. 13/176,036, filed on Jul. 5, 2011, now Pat. No. 8,857,446.

(30) Foreign Application Priority Data

Dec. 9, 2010 (CN) .......................... 2010 2 0650584

(51) Int. Cl.
*A24F 47/00* (2006.01)
*A61M 15/06* (2006.01)

(52) U.S. Cl.
CPC ............ *A24F 47/008* (2013.01); *A61M 15/06* (2013.01)

(58) Field of Classification Search
CPC .... A61M 15/06; A24F 47/00; A24F 47/004; A24F 47/008
See application file for complete search history.

(56) References Cited

U.S. PATENT DOCUMENTS

| 2011/0159723 A1* | 6/2011 | Fukushima | H01R 13/6683 439/488 |
| 2015/0047660 A1* | 2/2015 | Liu | A24F 47/008 131/329 |
| 2015/0090278 A1* | 4/2015 | Schiff | A24F 47/008 131/328 |
| 2015/0101625 A1* | 4/2015 | Newton | H05B 1/0244 131/329 |

FOREIGN PATENT DOCUMENTS

CN 203415645 U * 1/2014 ........... A24F 47/008

* cited by examiner

*Primary Examiner* — Anthony Calandra
(74) *Attorney, Agent, or Firm* — Cheng-Ju Chiang

(57) ABSTRACT

An electronic cigarette comprises an atomizer and a battery component connecting with the atomizer at one end thereof. The battery component comprises a battery sleeve, a rechargeable battery received in the battery sleeve, a battery seat disposed at the other end of the battery component opposite to the one end thereof to connect with the atomizer, and a pneumatic switch disposed in the battery component to electrically connect between the rechargeable battery and the atomizer. An opening is formed at a distal end of the battery seat facing away from the atomizer to allow electrical connection between a power supply and the rechargeable battery extending through the opening. The pneumatic switch is responsive to air flowing in the battery component so as to control electrical connection between the rechargeable battery and the atomizer and start the atomizer based on the air flowing.

7 Claims, 5 Drawing Sheets

ELECTRONIC CIGARETTE FOR CONVENIENT BATTERY CHARGING AND ATOMIZER STARTING

CROSS-REFERENCE TO RELATED APPLICATION

This application is a continuation-in-part of U.S. patent application Ser. No. 13/176,036, filed Jul. 5, 2011, priority of the filing date of which is hereby claimed under 35 U.S.C. §120, and which claims the priority benefit of Chinese Patent Application No. 201020650584.4, filed on Dec. 9, 2010, the contents of which are incorporated by reference herein in their entirety for all intended purposes.

BACKGROUND OF THE INVENTION

1. Field of the Invention

The invention relates to an electronic cigarette, in particular to an electronic cigarette having a simple structure and a convenient way to charge battery and to start its disposable atomizer by simply smoking.

2. The Related Arts

It's well known that smoking is harmful to one's health, but generally few of smokers can quit smoking as they have cigarette dependence and difficulty give it up. In view of this, an electronic cigarette is popular on markets, and is healthy for smokers and has no harm, and smokers can get the feeling of smoking, thereby being beneficial for quitting of smoking. But this product generally has the following disadvantages: inconvenient assembly and use, insufficient smoke amount, poor flowability of tobacco liquid, obvious bad smells produced during smoking, low efficiency and high labor cost.

SUMMARY OF THE INVENTION

The invention aims at providing an electronic cigarette, which can overcome the above mentioned defects of prior art, has a simple structure and a convenient way to use, including battery charging and starting its disposable atomizer by simply smoking.

For achieving above purposes, an electronic cigarette in accordance with the present invention comprises an atomizer and a battery component connecting with the atomizer at one end thereof. The battery component comprises a battery sleeve, a rechargeable battery received in the battery sleeve, and a battery seat disposed at the other end of the battery component opposite to the one end thereof to connect with the atomizer. An opening is formed at a distal end of the battery seat facing away from the atomizer to allow electrical connection between a power supply and the rechargeable battery extending through the opening.

Preferably, a positive electrode is formed at a central portion of the charging seat.

Preferably, a negative electrode is formed at side walls of the charging seat and surrounds the positive electrode.

Preferably, a pneumatic switch in response to air flowing is disposed in the battery component to control electrical connection between the rechargeable battery and the atomizer.

Further for achieving above purposes, an electronic cigarette in accordance with the present invention comprises an atomizer and a battery component connecting with the atomizer at one end thereof. The battery component comprises a battery sleeve, a rechargeable battery received in the battery sleeve, and a pneumatic switch disposed in the battery component to electrically connect between the rechargeable battery and the atomizer, the pneumatic switch being responsive to air flowing in the battery component so as to control electrical connection between the rechargeable battery and the atomizer and start the atomizer based on the air flowing.

Preferably, two connecting contacts are formed and extend from the pneumatic switch to electrically connect with the rechargeable battery and the atomizer.

Preferably, a sensor is formed and extends from the pneumatic switch to be located in an air path of air flowing within the battery component for sensing air flowing therein.

The present invention has the advantages of having a simple structure and a convenient way to use, including battery charging and starting its disposable atomizer by simply smoking.

DETAILED DESCRIPTION OF PREFERRED EMBODIMENT

Figure 1:
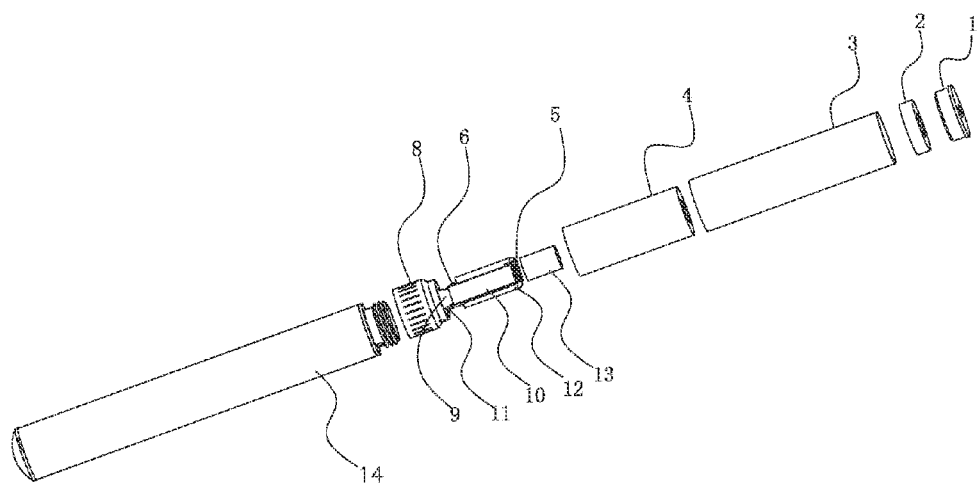
FIG. 1 is a breakdown drawing of the present invention.
Figure 2:
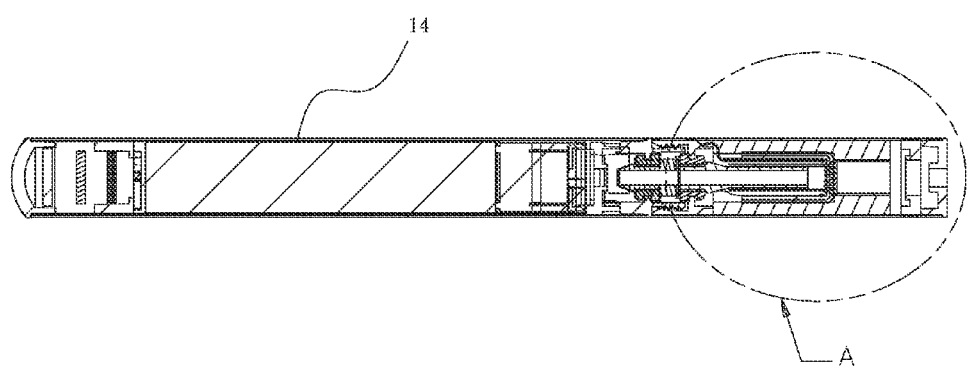
FIG. 2 is a sectional drawing of the utility mode.
Figure 3:
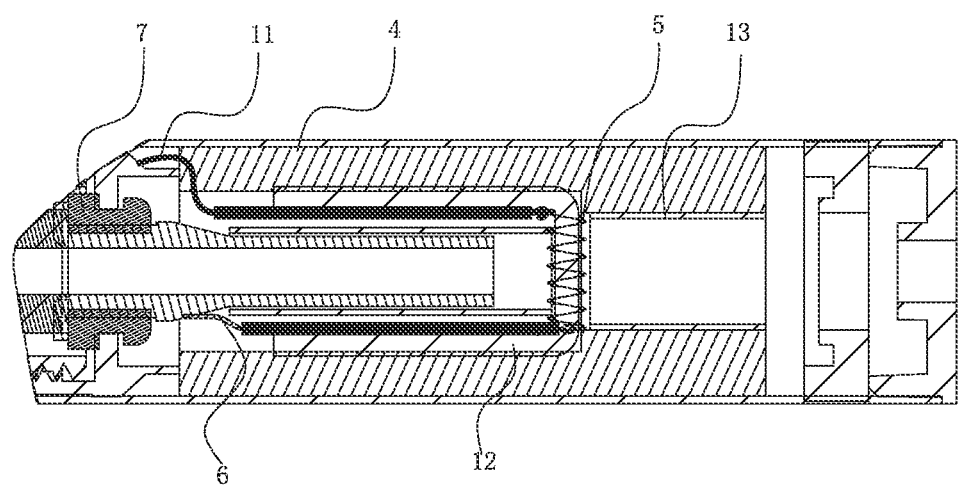
FIG. 3 is a partial enlarged drawing of A of FIG. 2.

For enabling those skilled in the art to better comprehend the present invention, the present invention is elaborated as follows by combining the drawings:

Refer to FIGS. 1-3. A disposable atomizer of an electronic cigarette comprises a battery component 14 and an atomizer, the atomizer comprises an atomizer cover 1, a rubber sleeve 2, an atomizer sleeve 3, a cotton 4, two wires 6 and 11, a heating wire 5, a rubber pad 7, a threaded sleeve 8, a propping pin 9, a first fibre pipe 10, a hollow fiber 12 and a second fibre pipe 13.

The heating wire 5 is connected at one end of each of the two wires 6 and 11, the other end of the wire 6 is fixedly connected with the propping pin 9, and the other end of the wire 11 is fixedly connected with the threaded sleeve 8; the heating wire 5 and the hollow fiber 12 are wound around together; the first fibre pipe 10 is arranged in the hollow fiber 12, the second fibre pipe 13 and the first fibre pipe 10 are coaxially arranged, and the second fibre pipe 13 is positioned behind the first fibre pipe 10; the hollow fiber 12 and the second fibre pipe 13 are both arranged in the cotton 4; the cotton 4 and the threaded sleeve 8 are both arranged in the atomizer sleeve 3; the atomizer cover 1 is arranged at a tail end of the atomizer sleeve 3; and the rubber sleeve 2 is arranged in the atomizer sleeve 3 and positioned between the second fibre pipe 13 and the atomizer cover 1.

The hollow fiber 12 is wound into a U shape, and the heating wire 5 is wound on a bottom part of the hollow fiber 12.

The rubber sleeve 2 is a silicone sleeve, and the rubber pad 7 is a silicone pad.

The rubber pad 7 is arranged outside the propping pin 9, and is positioned inside the threaded sleeve 8.

Each of two ends of the hollow fiber 12 contacts with the cotton 4.

The propping pin 9 is arranged at one end of the threaded sleeve 8, and extends into the first fibre pipe 10.

The manufacturing process of the present invention is elaborated as follows:

1. The heating wire 5 is welded with the connection bending circular positions of the wires 6 and 11 using a soldering iron, respectively;
2. The heating wire 5 is wound on the hollow fiber 12;
3. The wire 6 is welded on an edge of the propping pin 9 using the soldering iron, and the wire 11 is welded on an edge of the threaded sleeve 8 using the soldering iron;
4. the propping pin 9 is wrapped using the cotton 4, and simultaneously, the first fibre pipe 10 and the second fibre pipe 13 are wrapped inside the cotton 4 when the cotton 4 wraps the propping pin 9 for a circle, and the screw rod with the cotton 4 arranged is mounted in the atomizer sleeve 3;
5. The threaded sleeve 8 is pressed into the atomizer sleeve 3 using a die cutting machine;
6. Tar is injected into the surface of the cotton 4 via a needle head of an injector after the injector is filled with tar; and
7. The rubber sleeve 2 with a groove is parallelly mounted in the atomizer sleeve 3, and the atomizer cover 1 is pressed into the atomizer sleeve 3 using a punch.

Figure 4:
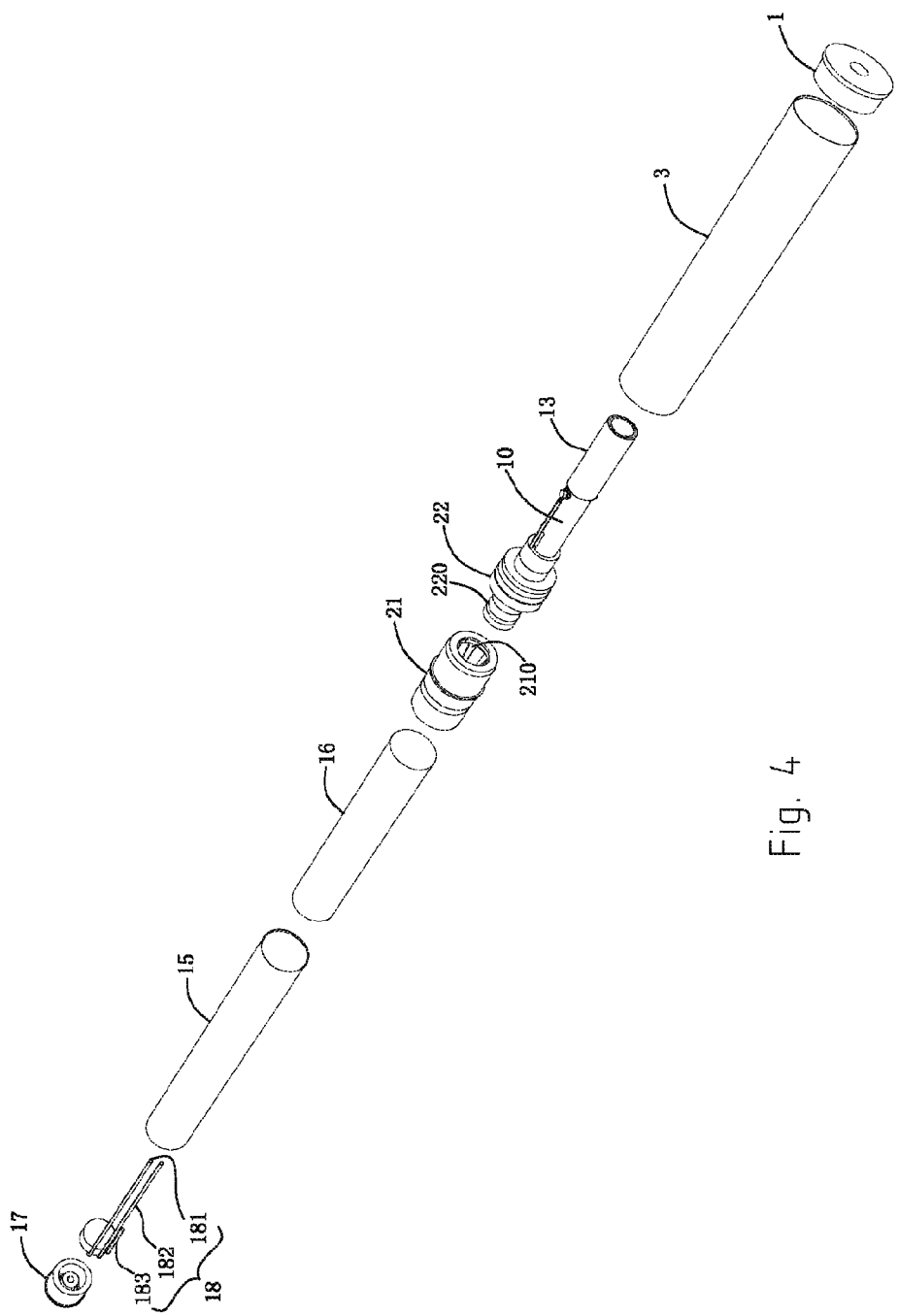
FIG. 4 is an exploded view of a second embodiment in accordance with the present invention.
Figure 5:
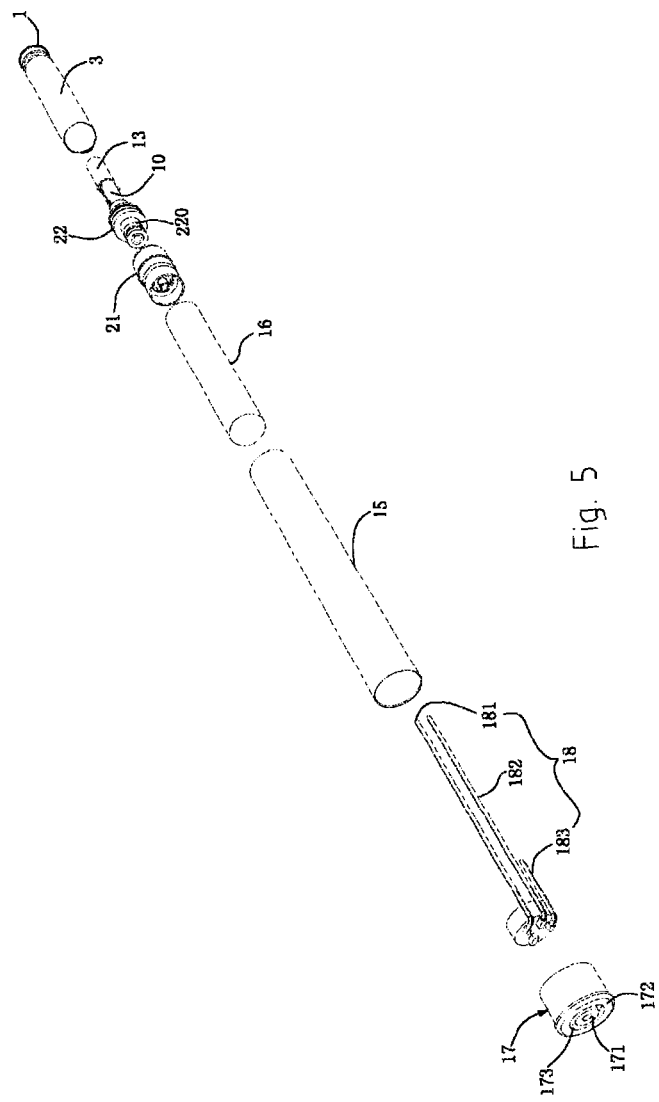
FIG. 5 is an exploded view of the second embodiment in accordance with the present invention, viewing from a different viewing angle.
Figure 6:
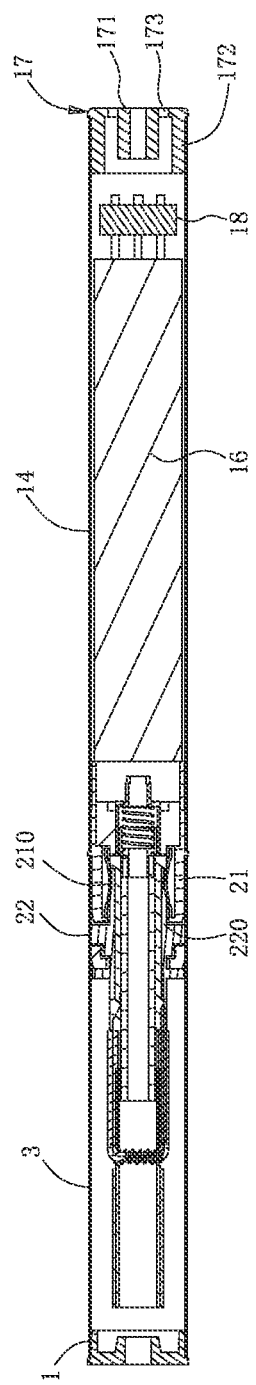
FIG. 6 is a sectional view of the second embodiment in accordance with the present invention.

Further referring to FIGS. 4-6, a second embodiment in accordance with the present invention is disclosed. Most parts in the second embodiment are similar to the ones in the previously disclosed embodiment. In the second embodiment, the battery component 14 of the electronic cigarette further comprises a battery sleeve 15 to receive a rechargeable battery 16 therein. A first connecting component 21 is disposed at an end of the battery component 14 to engage and electrically connect with the rechargeable battery 16. The first connecting component 21 is a hollow tube structure, and comprises at least one leaf spring 210 is formed at an inner wall of the first connecting component 21 and protrudes into a hollow inner space within the first connecting component 21. A second connecting component 22 is disposed at an end of the disposable atomizer of the electronic cigarette. A circular groove 220 is formed at a distal end of the second connecting component 22. When the disposable atomizer is about to connect with the battery component 14, the second connecting component 22 is inserted into and engaged with the first connecting component 21. In the meantime, the at least one leaf spring 210 of the first connecting component 21 is engaged with the circular groove 220 of the second connecting component 22 so as to fix the first connecting component 21 to the second connecting component 22 and to further rapidly connect the disposable atomizer with the battery component 14. Unlike screwing adopted in the previously disclosed embodiment, connection of the disposable atomizer and the battery component 14 becomes convenient and time saving.

Further referring to FIGS. 4-6, a charging seat 17 is disposed at the other end of the battery component 14 opposite to the first connecting component 21. A positive electrode 171 is formed at a central portion of the charging seat 17, and a negative electrode 172 is formed at side walls of the charging seat and surrounds the positive electrode 171. An opening 173 for battery charging is formed at a distal end of the charging seat 17 facing away from the battery component 14, and is ring-shaped to entirely surround the positive electrode 171 so as to electrically insulate the positive electrode 171 from the negative electrode 172. The opening 173 is further spatially communicable with an air path or an annular space residing between the rechargeable battery 16 and the battery sleeve 15. A power supply is able to electrically connect with the charging seat 17 in a convenient and rapid way so that the rechargeable battery 16 can be directly charged in the battery component 14 without being dismantled away from the battery component 14 or the disposable atomizer.

Further referring to FIGS. 4-6, a pneumatic switch 18 is disposed in the battery component 14. Preferably, the pneumatic switch 18 is disposed between the charging seat 17 and the rechargeable battery 16. The pneumatic switch 18 is electrically connected to the rechargeable battery 16 via two connecting contacts 181, 182 to control an electrical connection of the rechargeable battery 16 with the disposable atomizer. A sensor 183 is formed at and extends out of the pneumatic switch 18. The sensor 183 is located in the air path formed between the rechargeable battery 16 and the battery sleeve 15 in the battery component 14. When a user smokes the electronic cigarette, air flows from the opening 173 of the charging seat 17 into the air path in the battery component 14 toward the disposable atomizer due to inhaling pressure caused by the user. The sensor 183 of the pneumatic switch 18 senses air flowing and responds a signal to switch on electrical connection of the rechargeable battery 16 with the disposable atomizer and provide electrical power to start the disposable atomizer. As a result, the electronic cigarette can be smoked by the user right away without using any waiting time or operative time to start the atomizer.

Disclosed above is only a specific embodiment of the present invention. However, the present invention is not intended to limit as depicted above. Any technical person skilled in the technical art can think of variations which are still covered and fallen within the inventive spirit of the present invention and the claimed scope as defined in the following claims.

What is claimed is:

1. An electronic cigarette, comprising:
   an atomizer; and
   a battery component connecting with the atomizer at one end thereof, the battery component comprising:
     a battery sleeve;
     a rechargeable battery received in the battery sleeve; and
     a battery seat disposed at the other end of the battery component opposite to the one end thereof to connect with the atomizer, an opening formed at a distal end of the battery seat facing away from the atomizer to allow electrical connection between a power supply and the rechargeable battery extending through the opening;
   wherein a positive electrode is formed at a central portion of the charging seat, a negative electrode is formed at side walls of the charging seat and surrounds the positive electrode, the opening is located between the positive electrode and the negative electrode to electrically insulate the positive electrode from the negative electrode;
   wherein a first connecting component is disposed at an end of the battery component to engage and electrically connect with the rechargeable battery, and comprises at least one leaf spring formed at an inner wall of the first connecting component, a second connecting component is disposed at an end of the atomizer and comprises a circular groove formed at a distal end of the second connecting component, the second connecting component is inserted into and engaged with the first connecting component via engagement between the at least one leaf spring and the groove.

2. The electronic cigarette according to claim 1, wherein a pneumatic switch in response to air flowing is disposed in the battery component to control electrical connection between the rechargeable battery and the atomizer.

3. The electronic cigarette according to claim 1, wherein the opening is ring-shaped to surround entirely the positive electrode.

4. The electronic cigarette according to claim 1, wherein the opening is spatially communicable with an air path formed between the rechargeable battery and the battery sleeve.

5. An electronic cigarette, comprising:
an atomizer; and
a battery component connecting with the atomizer at one end thereof, the battery component comprising:
  a battery sleeve;
  a rechargeable battery received in the battery sleeve; and
  a pneumatic switch disposed in the battery component to electrically connect between the rechargeable battery and the atomizer, the pneumatic switch being responsive to air flowing in the battery component so as to control electrical connection between the rechargeable battery and the atomizer and start the atomizer based on the air flowing;
wherein a sensor is formed and extends from the pneumatic switch and the sensor is located in an annular space formed between the rechargeable battery and the battery sleeve for sensing air flowing therein.

6. The electronic cigarette according to claim 5, wherein two connecting contacts are formed and extend from the pneumatic switch to electrically connect with the rechargeable battery and the atomizer.

7. The electronic cigarette according to claim 5, wherein a first connecting component is disposed at an end of the battery component to engage and electrically connect with the rechargeable battery, and comprises at least one leaf spring formed at an inner wall of the first connecting component, a second connecting component is disposed at an end of the atomizer and comprises a circular groove formed at a distal end of the second connecting component, the second connecting component is inserted into and engaged with the first connecting component via engagement between the at least one leaf spring and the groove.

* * * * *